United States Patent
Aella et al.

(10) Patent No.: US 10,353,908 B1
(45) Date of Patent: Jul. 16, 2019

(54) PERSONALIZED SMART PROVIDER SEARCH

(71) Applicant: Anthem, Inc., Indianapolis, IN (US)

(72) Inventors: Lakshmi Manohar Aella, Naperville, IL (US); Adarsh Ramesh, Schaumburg, CT (US); Gregory Andrew Allard, East Lyme, CT (US); Shawn Wang, Kildeer, IL (US); Ariel Bayewitz, Teaneck, NJ (US)

(73) Assignee: ANTHEM, INC., Indianapolis, IN (US)

( * ) Notice: Subject to any disclaimer, the term of this patent is extended or adjusted under 35 U.S.C. 154(b) by 0 days.

(21) Appl. No.: 16/234,918

(22) Filed: Dec. 28, 2018

Related U.S. Application Data

(60) Provisional application No. 62/759,919, filed on Nov. 12, 2018.

(51) Int. Cl.
*G06F 16/24* (2019.01)
*G06F 16/2457* (2019.01)
*G06N 20/00* (2019.01)
*G06F 16/9535* (2019.01)

(52) U.S. Cl.
CPC .... *G06F 16/24578* (2019.01); *G06F 16/9535* (2019.01); *G06N 20/00* (2019.01)

(58) Field of Classification Search
CPC .......... G06F 16/24578; G06F 16/9535; G06N 20/00
See application file for complete search history.

(56) References Cited

U.S. PATENT DOCUMENTS

| | | | |
|---|---|---|---|
| 2011/0179081 A1* | 7/2011 | Ovsjanikov | G06N 5/04 707/780 |
| 2018/0018429 A1* | 1/2018 | Rice | G06Q 50/22 |

\* cited by examiner

*Primary Examiner* — Kristopher Andersen
(74) *Attorney, Agent, or Firm* — Morgan Lewis & Bockius LLP

(57) ABSTRACT

In one aspect there is a method for recommending one or more providers to a member. The method may comprise at a server, receiving, from a member computing device via a provider search interface, a provider request including a member identifier and member specified criteria. Retrieving one or more provider identifiers for association with the member specified criteria. Retrieving one or more member characteristics for association with the member identifier. For each provider identifier, retrieving one or more provider characteristics for association with the provider identifier. Analyzing the member characteristics and the provider characteristics to generate an ordered list of the providers, wherein the ordered list of the providers is based upon a relevancy rank of each provider that is specific to the member, wherein the relevancy rank is a function of at least one of: a provider cost factor, a provider quality factor, or a weighted combination thereof. Transmitting the ordered list of the providers to the member computing device via the provider search interface.

24 Claims, 7 Drawing Sheets

|    | Diabetes | COPD | Heart Condition | Obesity |
|----|----------|------|-----------------|---------|
| M1 | 1        | 0    | 0               | 1       |
| M2 | 0        | 1    | 0               | 0       |
| M3 | 0        | 0    | 1               | 0       |
FIG. 3A
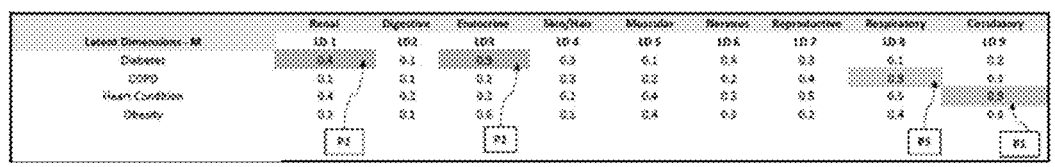
FIG. 3B
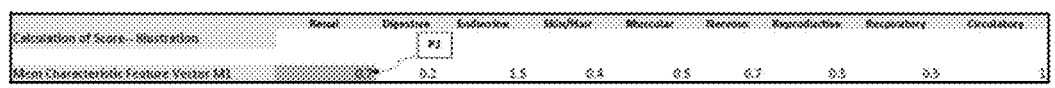
FIG. 3C
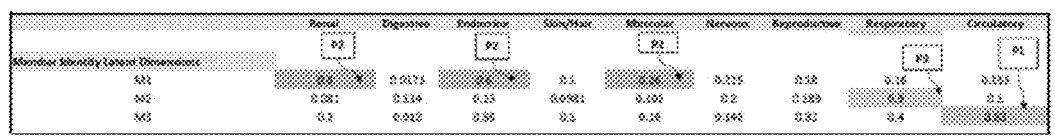
FIG. 3D
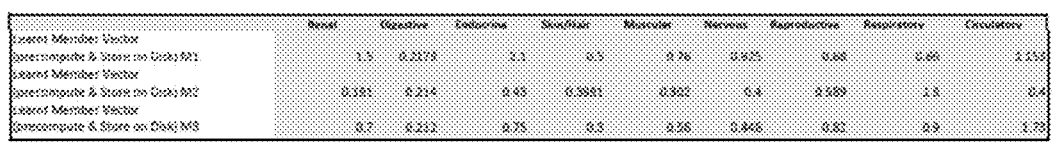
FIG. 3E

| Interaction Features | # WebClicks on the provider Web Page | # Times provider was seen in top 50 results in the past searches | #Historic Visits to Provider of Same Specialty |
|---|---|---|---|
| M1-P1 | 3 | 7 | 0 |
| M1-P2 | 1 | 5 | 3 |
| M1-P3 | 4 | 6 | 0 |
| M2-P1 | 4 | 5 | 1 |
| M2-P2 | 7 | 7 | 0 |
| M2-P3 | 5 | 8 | 3 |
| M3-P1 | 7 | 5 | 2 |
| M3-P2 | 6 | 6 | 1 |
| M3-P3 | 5 | 7 | 1 |

FIG. 3K

| Learnt Interaction Weights | |
|---|---|
| # WebClicks on the provider Web Page | 0.0027 |
| # Times providers was seen in top 50 results in the past searches | 0.0054 |
| #Historic Visits to Provider of Same Specialty | 0.0189 |

FIG. 3L

| | |
|---|---|
| Member Bias | |
| M1 | 0.00171 |
| M2 | 0.0021 |
| M3 | 0.223 |
| Provider Bias | |
| P1 | 0.0013 |
| P2 | 0.018 |
| P3 | 0.00167 |

FIG. 3M

Bias terms and Interaction Features

| | |
|---|---|
| Feature Bias | |
| Diabetes | 0.09 |
| COPD | 0.006 |
| Heart Condition | 0.09 |
| Obesity | 0.05 |
| | |
| Diabetes Volume | 0.001 |
| COPD Volume | 0.00342 |
| Heart Condition Volume | 0.00023 |

FIG. 3N

|    | Final Predicted Scores with Interaction features+Bias Terms | | Best Provider (for cost based model) |
|----|----|----|----|
| M1 | M1-P1 Score | 2.539905617 | |
|    | M1-P2 Score | 1.760720018 | P2 |
|    | M1-P3 Score | 2.381161953 | |
| M2 | M2-P1 | 1.329445787 | |
|    | M2-P2 | 1.178782517 | |
|    | M2-P3 | 1.178584694 | P3 |
| M3 | M3-P1 | 1.95167919 | P1 |
|    | M3-P2 | 2.451753186 | |
|    | M3-P3 | 1.965953782 | |

FIG. 3O

PERSONALIZED SMART PROVIDER SEARCH

CROSS-REFERENCE TO RELATED APPLICATIONS

This application claims the benefit of U.S. Provisional Patent Application No. 62/759,919 filed on Nov. 12, 2018 entitled "Personalized Smart Provider Search", which is incorporated by reference herein in its entirety.

BACKGROUND

With the ubiquity of the internet, it is now commonplace for users to conduct searches for a variety of products and services, including their medical providers (e.g., doctors, specialists, etc.) In various existing applications, these users (also referred to herein as members) searching for a provider in a search application for care are shown providers based on geographic proximity, ranked by some aggregated provider level cost efficiency or based on other aggregated measures specific to providers. However, this process does not ensure that the ranking is personalized for the individual member. For example, a member can have a combination of disease conditions, habits, and family history of diseases, or might have interacted with a certain set of providers, which resulted in successful maintenance of good health or well managed disease conditions, etc. Ranking providers only based on a general or highly aggregated subset high-level provider information (without taking granular member level information, provider level information or member provider interactions into account) can easily embed the right provider for the member in lower ranks and surface "sub-optimal" providers for the members on top.

Thus, there is a need for a provider search with predicting providers for an individual member given a member's conditions, past interaction history and information regarding how providers treated members with various conditions, along with volumes of patients they treated for these conditions, etc.

SUMMARY

Without limiting the scope of the appended claims, after considering this disclosure, and particularly after considering the section entitled "Detailed Description," one will understand how the aspects of various aspects are implemented and used to predict a score of relevancy across providers, for a given member.

In one aspect there is a method for recommending one or more providers to a member, the method comprising: at a server: receiving, from a member computing device via a provider search interface, a provider request including a member identifier and member specified criteria; retrieving one or more provider identifiers for association with the member specified criteria; retrieving one or more member characteristics for association with the member identifier; for each provider identifier, retrieving one or more provider characteristics for association with the provider identifier; analyzing the member characteristics and the provider characteristics to generate an ordered list of the providers, wherein the ordered list of the providers is based upon a relevancy rank of each provider that is specific to the member, wherein the relevancy rank is a function of at least one of: a provider cost factor and a provider quality factor; or a weighted combination thereof, transmitting the ordered list of the providers to the member computing device via the provider search interface.

In one aspect, analyzing the member characteristics and the provider characteristics includes: before receiving the provider request, precomputing a member vector and, for each provider, precomputing a respective provider vector.

In one aspect, wherein precomputing the member vector includes: arranging the member characteristics into a member characteristics vector; multiplying the member characteristics vector by a member feature matrix of learnt latent weights for each of the member characteristics to generate a member-characteristic-feature vector; summing the member-characteristic-feature vector and a learnt member parameters vector to generate a member vector; and storing the member vector.

In one aspect, precomputing a respective provider vector includes:
arranging the provider characteristics for the respective provider into a provider characteristics vector; multiplying the provider characteristics vector by a provider feature matrix of learnt latent weights for each of the provider characteristics to generate a provider-characteristic-feature vector; summing the provider-characteristic-feature vector and a learnt provider parameters vector to generate the respective provider vector; and storing the respective provider vector.

In one aspect, wherein analyzing the member characteristics and the provider characteristics includes: after receiving the provider request, retrieving the member vector and retrieving the respective provider vectors for each provider in a set of providers and for each provider in the set of providers: multiplying the member vector by the respective provider vector and adding the respective member-provider interaction weight to generate a respective member-provider score.

In one aspect, analyzing the member characteristics and the provider characteristics includes: summing the member-provider score and a feature bias value to update the member-provider score.

In one aspect, analyzing the member characteristics and the provider characteristics includes: ranking the providers based on the member-provider score for each of the respective providers.

In one aspect, member characteristics include at least one of, but not limited to: previous conditions, previous diagnoses, previous procedures, member demographics, age, gender, prescription information, over-the-counter medication history, habits, search history, member interactions with a provider search interface, zip code, number of hospitalizations in a past time period, and family history.

In one aspect, provider characteristics include at least one of, but not limited to: volume of patients seen, types of disease conditions seen, patient-submitted ratings, language, number of patients seen for each of the types of disease condition, quality of care for each of the types of disease condition, age, gender, years of practice, interactions with the member, and cost.

In one aspect, member-provider interaction characteristics include at least one of, but not limited to: web clicks for a particular provider by a member and historic visits to the particular provider by the member.

In one aspect, analyzing the member characteristics and the provider characteristics to generate a ranking of the providers includes:
For each of the providers, calculating a member-provider score:

$$\text{Score}(M, P) = \left(\sum_i \alpha_i * L_i^m + F_M\right)^T \left(\sum_j \beta_j * L_j^p + F_P\right) +$$
$$\sum_k \alpha_k B_k^m + \sum_l \beta_l B_l^p + B_M + B_P + \sum_n \gamma_n * I_n$$

wherein α is the features associated with the member,
wherein β is the features associated with the respective provider,
wherein $L_i^m$ are learnt latent parameters associated with the member feature i,
wherein $L_j^p$ are the learnt latent parameters associated with the respective provider feature j,
$F_M$ is the learnt parameters (vectors) associated with the member,
$F_P$ is the learnt parameters (vectors) associated with the respective provider,
$B_k^m$ is the characteristics bias terms that are learnt for the member feature k,
$B_l^p$ is the characteristics bias terms that are learnt for the respective provider feature l,
$B_M$ is the bias for the member,
$B_P$ are the bias for the respective provider,
$\gamma_n$ is the $n^{th}$ interaction feature,
$I_n$ is the learnt weight for the $n^{th}$ interaction feature contributing to the overall cost.

In one aspect, the member specified criteria includes at least one of: member location and member health conditions.

In one aspect, the ordered list of the providers is further based upon the member specified criteria.

BRIEF DESCRIPTION OF THE SEVERAL VIEWS OF THE DRAWINGS

The foregoing summary, as well as the following detailed description of aspects of the disclosed invention, will be better understood when read in conjunction with the appended drawings of an exemplary aspect. It should be understood, however, that the invention is not limited to the precise arrangements and instrumentalities shown.

In the drawings:

FIG. 3A is an exemplary illustration of a table having features of multiple members;

FIG. 3B is an exemplary illustration of a table having learnt latent vectors for member features;

FIG. 3C is an exemplary illustration of a table having a member characteristics feature vector;

FIG. 3D is an exemplary illustration of a table having member identity latent dimensions;

FIG. 3E is an exemplary illustration of a table having learnt member vectors;

FIG. 3K is an exemplary illustration of a table having interaction features for each member;

FIG. 3L is an exemplary illustration of a table having learnt interaction weights for each interaction feature;

FIG. 3M is an exemplary illustration of a table having individual member and individual provider biases;

FIG. 3N is an exemplary illustration of a table having biases for member and provider features;

FIG. 3O is an exemplary illustration of a table having predicted scores with interaction features and bias terms; and

DETAILED DESCRIPTION

Figure 1:
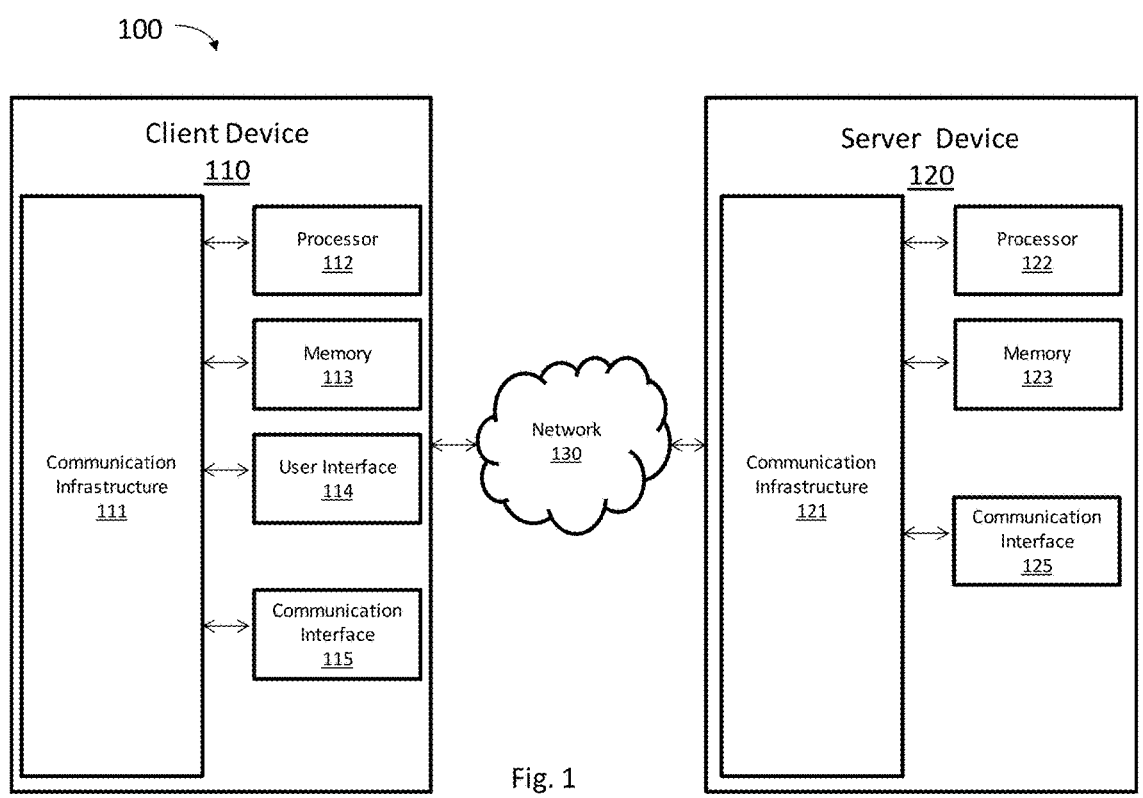
FIG. 1 illustrates a block diagram that illustrates an example system for improving login and registration efficiency to access data according to at least one aspect of the present invention.

In some aspects, methods and systems described herein provide a recommendation about the most-relevant providers for a given member in various contexts and based on a number of characteristics such as member specific characteristics, provider specific characteristics and/or member-provider interactions, among others described herein. The recommendation may include generation of a relevancy score across providers for a given member. The relevancy scores may indicate personalized success metrics for the member including cost and quality of care between a member and provider or any combination of such success measures for a member and provider. These relevancy scores may be used to rank the providers and provide more accurate results than conventional methods.

In some aspects, member characteristics (e.g., disease pre-conditions, previous interactions with providers, web interactions), provider characteristics (e.g., specialty area, cost, years of experience) and any of the past interactions between the member and provider may be used to predict scores of relevancy (cost based or any other success based measures) using a systematic algorithmic approach while performing searches using a minimal amount of time, as described below.

Previous provider search methods could not provide the same level of personalization, accuracy and efficacy as the aspects described herein without sacrificing speed in performing the search and/or quality in the search results. For example, consider a member with diabetes that is conducting a search for a provider. Just because a member has diabetes, identifying a provider who had some degree of success in treating diabetic patients, by a given metric, does not necessarily result in matching the optimal provider for that member. For example, the member may have had a negative interaction in the past with the provider and would not want to see that provider listed in future search results. In some aspects described herein, one or more systems may learn member characteristics based on, for example, the member's historical interactions with other providers such as personal visits, web-based interactions, the costs associated with member-level known information such as health/disease conditions, family history, past medications, over the counter drugs, habits, etc. Exemplary systems may also, simultaneously learn granular representations of providers based on the provider's interactions with the members along with the provider's individual features/characteristics. The systems may then use these learnt representations for members and providers to provide better search results to a member (e.g., search results that are more likely to lead to a successful outcome).

In some aspects, the systems may systematically and automatically receive as inputs several hundreds of factors of information associated with members as features, several hundreds of pieces of factors for providers and at the same time information related to member-provider historical interactions to compute a score for every provider specific to every member, while also providing timely search results to the member by summarizing/distilling the member information and their learnt representations to a pre-computed fixed dimensional vector, thus bounding the number of mathematical operations performed after a search request is received. This bounding is true even when the number of input features are several hundreds or thousands.

Exemplary predictions may include predicted cost for the member and/or provider, a quantified likelihood of a member's improved health after the interaction with the provider or any predefined measures, sets or combination success measures. In some aspects, the systems may be capable of fast inference of predictions in real-time. The approach systematically adapts to changes to data, which is required to predict an optimal set of providers (for instance, optimized for cost and/or quality).

The disclosed method may also be capable of predicting provider scores even when some of the member level features or provider level features are not available. Further, the method may be capable of predicting scores even when no explicit information (e.g., member/provider characteristics) is available for members or providers; the method may learn member and provider characteristics based on a member interacting with a set of providers in the past and also by utilizing information such as the members being treated by the provider. These predictions may be implemented by defining a loss function without the feature specific latent components associated with the member (provider) features described in further detail below, and by constraining the model to learn and predict from purely learnt latent factors for member, $F_M$. If provider features are not available then the model may be similarly optimized with pure provider latent components, $F_P$ without provider feature components.

In some aspects, even when explicit success metrics such as past costs, efficiency measures or quality of care measures between members and providers is not available, the method may infer member-provider scores using implicit information, member behavior including visit history, clicks on provider pages, browsing history, search patterns, or even mouse movements. Aspects may implement certain machine learning models to learn member and provider characteristics based on member/provider historical interactions and optimize a success metric in predicting the scores even without success metrics such as cost and efficiency. The machine learning functionality may be implemented by defining and optimizing a loss function defined on success metrics such as visit/click propensity or certain proxies for quality such as improved health status/condition after visit, among others that are not based on success factors such as cost.

Referring to the drawings in detail, wherein like reference numerals indicate like elements throughout, there is shown in the Figures, system and methods for improving provider search, generally designated, in accordance with an exemplary aspect of the present invention.

FIG. 1 shows a block diagram that illustrates a system 100 for improving personalized provider search according to at least one aspect of the present invention. While some example features are illustrated, various other features have not been illustrated for the sake of brevity and so as not to obscure pertinent aspects of the example aspects disclosed herein. To that end, in at least one aspect, the system 100 may include one or more computers or servers, non-transitory memory operable to store one or more computer programs and one or more processors to implement the one or more computer programs. For example, the system 100, shown in FIG. 1, may include client device 110, server device 120 and network 130.

Client device 110 may be a computing device for receiving inputs from a user (e.g., a member), requesting data from server device 120 via network 130 and/or displaying data from service device 120 at the request of a user. Examples of a client device 110 may include a smart phone, tablet or a personal computer, among others.

Server device 120 may be any computing device, including one or more software modules (e.g., a scoring module) for receiving and/or responding to requests for data from client device 110. Examples of data may include web page data, hypertext markup language (HTML), text, video, audio as a free form speech describing symptoms and conditions, picture, software, executable, interpretable, byte-code, and binary files. In some aspects, the server device 120 may be a plurality of computing devices that process the request from the client device 110. The server device 120 may be configured to process requests from other computing devices in parallel with the request from the client device 110.

In one aspect, server device 120 is a web server that hosts a website. Client device 110 may be configured to request provider recommendations from server device 120 based on a hypertext transfer protocol (HTTP). Server device 120 may respond to a provider recommendation request by sending provider recommendation data (e.g., an ordered list of providers) to client device 110. In one aspect, provider recommendation data may include web page data included on an HTML web page. While the server device 120 may be configured for HTTP/HTML requests and responses, as described in the exemplary aspect above, the system 100 is not limited to the use of HTML or HTTP, and that aspects of the present invention can be used with any computer communication language or network protocol suitable for the purposes of the described communications between client device 110 and server device 120.

Client device 110 may include communication infrastructure 111, processor 112, memory 113, user interface 114 and communication interface 115. Server device 120 may include communication infrastructure 121, processor 122, memory 123 and communication interface 125.

Processor 112 or processor 122 may be any type of processor, including but not limited to a special purpose digital signal processor. Processor 112 is connected to a communication infrastructure 111 (for example, a bus or network). Processor 112 is connected to a communication infrastructure 121 (for example, a bus or network). Various software implementations are described in terms of this exemplary computer system.

Memory 113 or memory 123 may include one or more of: random access memory (RAM), a hard disk drive and a removable storage drive, such as a floppy disk drive, a magnetic tape drive, or an optical disk drive, etc. The removable storage drive may read from and/or writes to a removable storage unit. The removable storage unit can be a floppy disk, a magnetic tape, an optical disk, etc., which is read by and written to a removable storage drive. Memory 113 and/or memory 123 may include a computer usable storage medium having stored therein computer software programs and/or data to perform any of the computing functions of client device 110 and/or server device 120. Computer software programs (also called computer control logic), when executed, enable client device 110 and/or server 120 to implement aspects of the present invention as discussed herein. Accordingly, such computer software programs represent controllers of client device 110 and/or server 120. Memory 123 may include one or more data stores that store data such as web page data, software files or any other types of data files. Server device 120 may retrieve the data from memory 123 before transmitting to client device 110 via network 130. Memory 123 may include member characteristics, provider characteristics, member-provider interaction characteristics, feature bias weightings, member/provider bias weightings, and learnt weightings, among other described herein.

User interface 114 may be produced by a program that controls a display (not shown) of client device 110. User interface 114 may include one or more peripheral user interface components, such as a keyboard or a mouse. The user may use the peripheral user interface components to interact with client device 110. User interface 114 may receive user inputs, such as mouse inputs or keyboard inputs from the mouse or keyboard user interface components. User interface 114 may display data, such as web pages, on the display of client device 110 using a web browser. While the user interface 114 may be configured for displaying data using a web browser, as described in the exemplary aspect above, user interface 114 is not limited to displaying data using a web browser, and that aspects of the present invention may contemplate using other display devices or software suitable for the purposes of the displaying the data.

Communication interface 115 and/or communication interface 125 allow data to be transferred between client device 110 and server device 120 via network 130. Examples of communication interface 115 or communication interface 125 may include a modem, a network interface (such as an Ethernet card), a communication port, a Personal Computer Memory Card International Association (PCMCIA) slot and card, etc. Data transferred via communication interface 115 or communication interface 125 are in the form of signals, which may be electronic, electromagnetic, optical, or other signals capable of being transmitted or received by communication interface.

Network 130 connects client device 110 and server device 120 by carrying signals. Network 130 may be implemented using wire or cable, fiber optics, a phone line, a wireless link, a cellular phone link, a radio frequency link, or any other suitable communication channel. For instance, network 130 may be implemented using a combination of channels. Network 130 may be implemented as an intranet and/or an internet.

Figure 2:
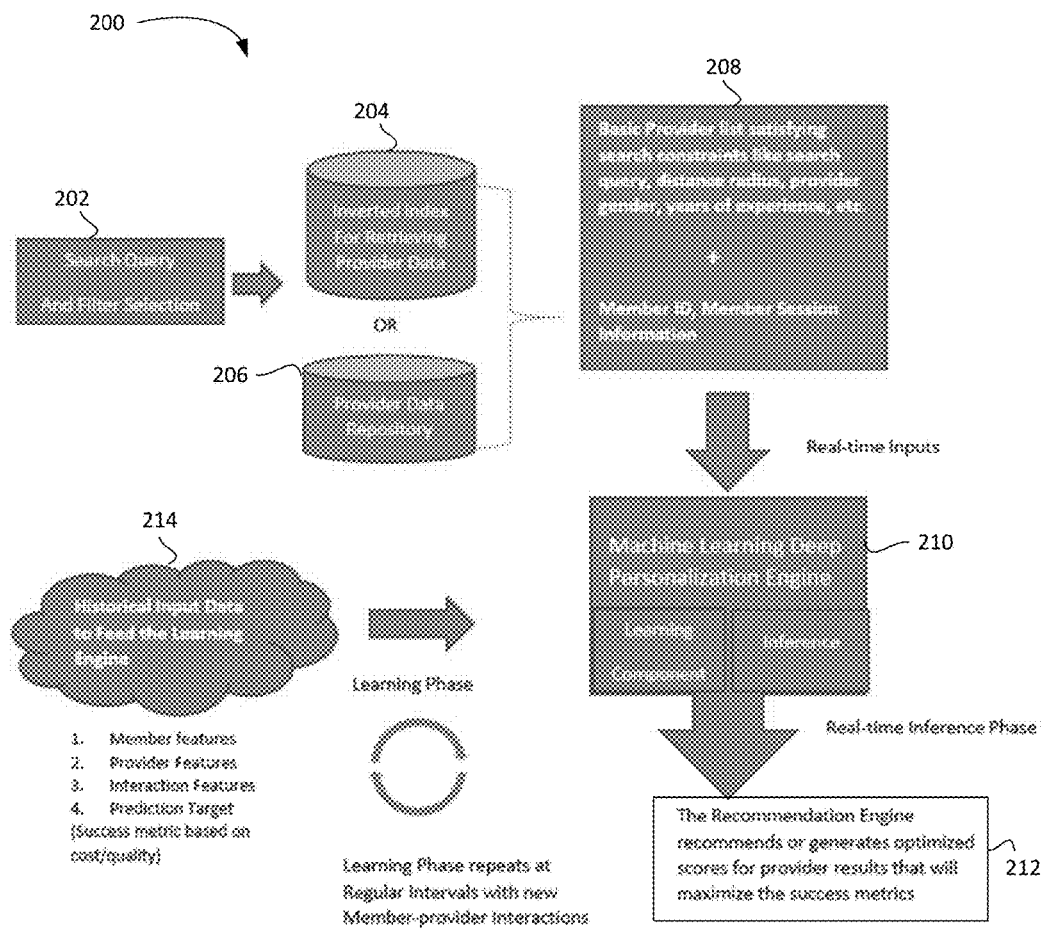
FIG. 2 is a flow chart for a method of recommending one or more providers to a member.

FIG. 2 illustrates a flow chart describing a method 200 for recommending one or more providers to a user. While some example features are illustrated, various other features have not been illustrated for the sake of brevity and so as not to obscure pertinent aspects of the example aspects disclosed herein. The method 200 may be implemented using the client device 110 and a scoring module of server device 120 of FIG. 1. However, in other aspects, other components may be utilized to implement one or more of the steps of method 200. FIGS. 3A-3P may also be referenced to describe at least some steps of the method 200.

The scoring module of server device 120 may be configured to receive (202), from a client device 110 (which may also be referred to herein as a user computing device), via a provider search interface (e.g., webpage), a provider request (e.g., search query). The provider request may be a request for an ordered or ranked list of providers that best satisfy the provider request criteria specified by the user. The provider request may include a member identifier that identifies the member submitting the request.

The scoring module of server device 120 may be configured to retrieve (204 and/or 206) one or more provider identifiers for association with the member specified criteria. In some aspects, for each provider identifier, server device 120 may be configured to retrieve indicia of one or more provider characteristics for association with the respective provider identifier. Examples of provider characteristics may include indicia of volume of patients seen, types of disease conditions seen, patient-submitted ratings, language, number of patients seen for each of the types of disease condition, quality of care for each of the types of disease condition, age, gender, years of practice, interactions with the member, and cost. Additional examples of provider characteristics may include indicia of the geographic location of the provider (e.g., zip codes), any characteristic of the geographic region of the provider, and hospital affiliations, among others. In some aspects, server device 120 may be configured to retrieve one or more member characteristics for association with the member identifier. Examples of member characteristics may include indicia of: previous conditions, previous diagnoses, previous procedures, member demographics, age, gender, prescription information, over-the-counter medication history, habits, search history, member interactions with a provider search interface, zip code, number of hospitalizations in a past time period, family history, and socio-demographics.

The provider request may include member specified criteria that may be utilized to reduce the number of recommended providers. Examples of member specified criteria may include indicia of member location and a suitable distance radius that the member would travel to visit the provider, member health conditions, provider gender, and/or provider years of experience, provider language, hospital affiliations, type of specialties or a primary specialty for the provider, subspecialties/clinical areas of interest and expertise of a provider, among others.

The member specified criteria may be utilized to filter the list of providers in the ordered list as described below. For example, server device 120 may associate (208) the ordered list of providers with the member specified criteria. For example, the server device 120 may associate (208) the ordered list of providers with the member specified criteria by filtering the list of providers based on the member specified criteria. In one aspect, the server device 120 may filter the list of providers that are within a member-specified distance radius from the member, provider gender, and/or provider years of experience, among other.

The scoring module of server device 120 may be configured to analyze (210), using a personalization and/or recommendation engine, the member characteristics and the provider characteristics to generate an ordered list of the providers. In some aspects, the ordered list of the providers is based upon a relevancy rank of each provider that is specific to the member. In some aspects, the relevancy rank is a function of a success metric. As used herein, a success metric is a factor that is optimized when ranking the providers for relevancy. Examples of a success metric may include indicia of cost, quality or a weighted combination of these measures. As used herein, quality can describe how well a member's health conditions are managed by the provider. In some aspects, a success metric may include a combination of visit/clicks of a provider's website by a member, so that the relevancy rank identifies providers that are likely to be clicked on a results page provided to the members, or those providers that have a higher visit likelihood. Examples of a success metric may include at least one indicia of: a provider cost factor, a provider quality factor, a provider efficiency factor, or a weighted combination thereof. The success metric may be associated with the time of the search (e.g., time of the year, season, month, etc). The method can learn factors responsible for driving these success measures based on time and apply these in inferring the score for member-provider. For example, in some aspects, time (e.g., season, month, etc.) can be used as the interaction features. The time/season/month and a suitable weight may be learnt by some aspects of the algorithm as it relates to the success measure (e.g., cost).

In some aspects, analyzing the member characteristics and the provider characteristics to generate an ordered list of the providers includes:

for each of the providers, calculating a member-provider score (e.g., relevancy rank) using the following equation (1):

$$\text{Score}(M, P) = \left(\sum_i \alpha_i * L_i^m + F_M\right)^T \left(\sum_j \beta_j * L_j^p + F_P\right) + \sum_k \alpha_k B_k^m + \sum_l \beta_l B_l^p + B_M + B_P + \sum_n \gamma_n * I_n$$

wherein M refers to the member associated with the provider search,
wherein P refers to the provider,
wherein $\alpha$ is the characteristics associated with the member,
wherein $\beta$ is the characteristics associated with the respective provider,
wherein $L_i^m$ are learnt latent parameters associated with the member feature i,
wherein $L_j^p$ are the learnt latent parameters associated with the respective provider feature j,
$F_M$ is the learnt parameters (vectors) associated with the member,
$F_P$ is the learnt parameters (vectors) associated with the respective provider,
$B_k^m$ is the characteristics bias terms that are learnt for the member feature k,
$B_l^p$ is the characteristics bias terms that are learnt for the respective provider feature l,
$B_M$ is the bias for the member,
$B_P$ are the bias for the respective provider,
$\gamma_n$ is the $n^{th}$ interaction feature,
$I_n$ is the learnt weight for the $n^{th}$ interaction feature contributing to the overall cost.

The characteristics $\alpha$ associated with the member may refer to member characteristics specific to the member. As shown above, the characteristics $\alpha$ are arranged in a vector, and may be referred to herein as a member-characteristic vector.

The characteristics $\beta$ associated with the respective provider may refer to provider characteristics specific to each provider. As shown above, the characteristics $\beta$ are arranged in a vector, and may also be referred to herein as a provider-characteristic vector.

The learnt parameters $L_i^m$ associated with a success metric model may refer to the weightings applied to the member characteristics. The learnt parameters $L_j^p$ associated with a success metric model may refer to the weightings applied to the provider's characteristics. Each success metric may have a corresponding model with specific weightings that can be applied to the member characteristics or provider characteristics respectively. The model used for scoring may be specified by the member. By using different models for each success metric, different factors (e.g., providers that cost less, or providers with more experience) can be accentuated or attenuated in the final score to rank the providers accordingly as personalized to the member conducting the search. The learnt parameters may be organized in a vector or matrix for easier combination with member or provider characteristics.

The member learnt parameters vector $F_M$ may refer to weightings for latent factors learnt from data for the identity of the member M. Similarly the provider learnt parameters vector $F_P$ may refer to latent factors learnt from data for the identity of the provider P. The member and provider learnt parameters may specify how a specific member or provider contributes to the overall score in addition to the contributions of their characteristic/feature values.

The member-feature bias vector may refer to the weightings applicable to the member characteristics. The provider-feature bias vector may refer to the weightings applicable to the provider characteristics. These member and provider feature biases may be scalar weights applied to individual member features. For instance, the member and provider feature biases may represent the direct numeric weight that can be applied to a user feature indicating a heart disease that contributes to the overall cost.

The member bias $B_M$ may refer to the weightings specific to the member. The provider bias $B_P$ may refer to the weightings specific to the respective provider. In other words, the weightings in the member and provider biases may change for each particular member or provider. For example, a provider that is prominent in their field may have a higher weighting than a provider that is a new graduate. In another example, a provider that charges less for services than another provider may also have a higher weighting.

The interaction features $\gamma$ may refer to the numerical values associated with each member-provider interaction. Examples of member-provider interactions include indicia of member visits to the provider, number of times a provider showed up in the past in the member's search results, number of clicks/page views on a provider's link in the past by the member, time spent (e.g., browse time) on a provider's webpage, mouse-overs on a provider's webpage, and number of prescriptions filled that were written by a provider, and browse patterns in historical session logs, among others.

The learnt interaction feature weight $I_n$ may refer to the weightings specific to the member-provider interactions. For example, member visits to the provider may have a higher weighting than member clicks on a provider website. In this example, member visits to the provider may have a greater impact on the final provider rankings than member clicks.

The scoring module of server device 120 may be configured to calculate (210) the learnt variables described herein using historical member, provider and/or interaction data. In some aspects, the historical member, provider and interaction data, along with a success metric may be input into a machine learning algorithm to optimize an objective function and learn the variable weights suitable for ranking providers. A suitable objective function may be defined as a mathematical equation that maximizes a designated success metric (e.g., low cost, high quality of care) using the feature values (e.g., historical member, provider and/or interaction data) and unknown parameters (latent vectors, feature weights and biases) that are to be learnt. Examples of machine learning algorithms to learn the unknown parameters may include gradient based class of algorithms such as stochastic gradient descent, mini-batch gradient descent to learn model parameters or matrix factorization algorithms.

The machine learning algorithm may be reapplied at regular intervals, or as more historical data is received to update the learnt variable weights.

In some aspects, portions of equation (1) may be precomputed to reduce the time for calculating a respective score after receiving a provider request from the member. For example, instead of computing expressions for each member and provider pair separately at the time of real-time prediction (e.g., after receiving a provider request from the member), the server device 120 may compute the matrix representation of the entire factor for the member specific components and store them as a compact NumPy matrix. As used herein, NumPy may refer to a python library for representing large multi-dimensional arrays and matrices and a collection of mathematical functions to operate on these. If $M_{All}$ is the matrix of member features for all the members then the server device 120 may pre-compute the following matrix multiplication $M_{All}*L^m$ followed by the addition of the member factor matrix. The final member matrix may be stored in memory as a serialized data structure. Similarly, the server device 120 may pre-compute the provider side of operations and store the resultant values in a provider matrix. Each row of the member matrix may correspond to one of the members and may be used in computing in the final provider score. The mapping between the member the member matrix rows and the member identity (e.g., member identifier, MCID) may be stored in a separate fast lookup dictionary. The provider level components may also be similarly stored and accessed. Similar type of precomputations may be performed on the interaction terms and feature bias level terms as well in some aspects. By performing the precomputation, the final scoring for a member provider pair may only involve H multiplications, where H is the number of latent dimensions in the learnt parameters $L_i^m$ and $L_j^p$. This may significantly reduce the basic computation time to a significant degree. For example, without precomputation, the above score would take approximately 0.3 or more seconds to compute 500 provider scores. With precomputation, the above score may be calculated in approximately 0.01 seconds. By constructing the member side and provider side components separately before the search request, it can be ensured that the computation time is also not dependent on the number of member features or the number of provider features. Such a configuration will enable significantly faster computation of real-time predictions even when there may be thousands of member and provider features (or hundreds of thousands of features). In some embodiments, the number of member, provider and/or member-provider interaction features may be greater than 10, greater than 20, greater than 50, greater than 100, greater than 500, greater than 1000, greater than 10,000, greater than 100,000 or greater than 1,000,000.

The memory footprint of the one or more models may also be reduced by compactly representing the integrated matrix models described above. Also, these integrated member and provider matrix representations (e.g., in NumPy) can be shared across multiple worker processes that can independently process a request for recommendations or predictions. This further achieves parallelization of requests, and reduces server response time, while foregoing replicating the models for parallel working units (different worker processes).

In some aspects, before receiving the provider request, the scoring module of server device 120 is configured to precompute a member vector A, where $$A = \left(\sum_i \alpha_i * L_i^m + F_M\right)$$

of equation (1). In some aspects, the server device 120 precomputes the member vector A by arranging the member characteristics into a member characteristics vector α. FIG. 3A illustrates a table representing a member characteristics vector. M1, M2 and M3 may refer to member 1, member 2 and member 3. Each member may have unique member characteristics or member features that are characterized by medical histories, geographical preferences, etc. A member characteristic may be any characteristic that is representative of a specific member. FIG. 3A reflects specific medical histories for M1, M2 and M3 for diabetes, chronic obstructive pulmonary disease (COPD), heart condition, and obesity. As shown, member 1 may be suffering from diabetes and obesity (reflected by the 1 under diabetes and obesity for M1). In a similar manner, FIG. 3A also shows that member 2 (e.g., M2) may have COPD and member 3 (e.g., M3) may have a heart condition. If a member is not suffering from a particular condition, then a 0 may be used for that condition for that respective member. For example, member 1 (e.g., M1) may not be suffering from COPD (e.g., since M1 has a 0 represented under COPD).

In some aspects, the scoring module of server device 120 is configured to precompute a member vector A by multiplying the member characteristics vector (e.g., member characteristics vector shown in FIG. 3A) by a member feature matrix of learnt latent weights $L^m$ for each of the member characteristics to generate a member-characteristic-feature vector. FIG. 3B illustrates a table showing a member feature matrix of learnt latent weights. Member features shown in FIG. 3B may be the same member features shown in FIG. 3A, which are diabetes, COPD, heart condition and obesity. The table in FIG. 3B may include latent dimensions associated with each member feature. Latent dimensions, and the number thereof, may be pre-specified in a machine learning algorithm to generate the learnt latent weights. In FIG. 3B, the latent dimensions may define specific physiological systems including the renal system, digestive system, endocrine system, skin/hair systems, muscular system, nervous system, reproductive system, respiratory system and circulatory system. LD 1 may indicate latent dimension 1 which may be the renal system, LD 2 may indicate latent dimension 2 which may be the digestive system, and so on. Each physiological system may have a score from 0 to 1 indicating the relationship the particular physiological system may have as it relates to each member feature, provider feature, provider identity and member identity. A value closer to 1 (e.g., a higher value) may indicate a stronger relationship between the physiological system and member feature. For example, latent dimension 9, circulatory, has a score of 0.9 for member feature, heart condition. This may indicate that the circulatory system has a strong relationship with patients that have heart conditions. This may also indicate that patients with heart conditions have a strong relationship with conditions related to the circulatory system. Similarly, latent dimension 9, circulatory system, may have a score of 0.2 for diabetes which may mean that the circulatory system has a weak relationship with individuals that are diabetic. This may also indicate that patients suffering from diabetes have a weak relationship with conditions related to the circulatory system. Referring to FIG. 3C, there is shown a table representing member characteristics feature vector for M1. The member characteristics feature vector may illustrate the result of multiplying the member characteristics vector (e.g., FIG. 3A) by the member feature matrix of learnt latent weights (e.g. FIG. 3B).

In some aspects, the scoring module of server device 120 is configured to precompute the member vector A by summing the member-characteristic-feature vector (e.g. 3C) and a learnt parameters vector (e.g., 3D) to generate the member vector, as shown in FIG. 3E. The server device 120 may then store the member vector A for later use after a request is received. As discussed above, FIG. 3C shows a table representing member characteristics feature vector for M1. FIG. 3D may illustrate a table representing member identity learnt parameters vectors for individual members (e.g., M1, M2 and M3 also described in FIG. 3A). In this example, the greater the number, the greater the correlation between latent dimensions and the respective member. For example, member 3 may have a strong relationship with the circulatory system, as shown by 0.83 whereas member 2 may have a weak relationship with the circulatory system as shown by 0.1. Also, member 1 may have a strong relationship with the renal system indicated by a value of 0.80 whereas member 2 may have a weak relationship with the renal system indicated by a value of 0.081. Member 1 may also have a strong relationship with the endocrine system indicated by a value of 0.6. The server device 120 may precompute the member vector A for member 1 by summing the table representing member characteristics feature vector for M1 in FIG. 3C with the row corresponding to the learnt parameters vector for M1 from the table in FIG. 3D. In FIG. 3E, the row corresponding to M1 in the table illustrates the result of summing the member characteristics feature vector for M1 in FIG. 3C with the learnt parameters vector for M1 in FIG. 3D.

In some aspects, before receiving the provider request, for each provider: the scoring module of server device 120 precomputes a respective provider vector B, where $$B = \left(\sum_j \beta_j * L_j^p + F_P\right)$$

of equation 1.

Figures 3F, 3G, 3H, 3I, 3J:
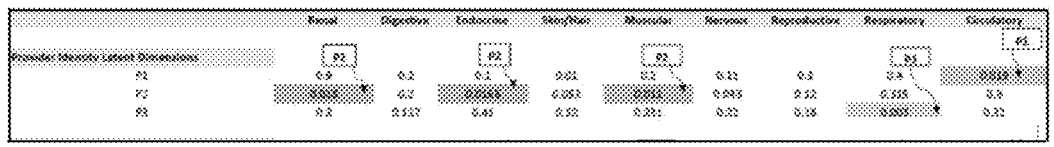
FIG. 3F is an exemplary illustration of a table having features of multiple providers.
FIG. 3G is an exemplary illustration of a table having learnt latent vectors for provider features.
FIG. 3H is an exemplary illustration of a table having a provider characteristics feature vector.
FIG. 3I is an exemplary illustration of a table having provider identity latent dimensions.
FIG. 3J is an exemplary illustration of a table having learnt provider vectors.

In some aspects, the scoring module of server device 120 precomputes the provider vector B by arranging the provider characteristics for the respective provider into a provider characteristics vector β. FIG. 3F illustrates a table representing a provider characteristics vector. P1, P2 and P3 may refer to Provider 1, Provider 2 and Provider 3. In this example, the provider characteristics include Diabetes patient volume, COPD patient volume and Heart Condition patient volume (shown in the 1000s). As shown in FIG. 3F, provider 3 has the highest volume of patients with Diabetes at 0.025 and the highest volume of patients with COPD at 0.008. Provider 2 has the highest volume of patients with a Heart Condition at 0.004.

In some aspects, the scoring module of server device 120 precomputes the provider vector B by multiplying the provider characteristics vector P by a provider feature matrix of learnt latent weights $L^p$ for each of the provider characteristics to generate a provider-characteristic-feature vector. FIG. 3G illustrates a table showing a provider feature matrix of learnt latent weights. Provider features shown in FIG. 3G may be the same provider features as shown in FIG. 3F, which are Diabetes volume, COPD volume and Heart Condition volume. The table may include latent dimensions. The number of latent dimensions may be pre-specified by an analyst while generating the learnt latent weights using machine learning. In FIG. 3G, the latent dimensions may define specific physiological systems including the renal system, digestive system, endocrine system, skin/hair systems, muscular system, nervous system, reproductive system, respiratory system and circulatory system. LD 1 may indicate latent dimension 1 which may be the renal system, LD 2 may indicate latent dimension 2 which may be the digestive system, and so on. Each physiological system may have a score from 0 to 1 indicating the relationship the particular physiological system may have as it relates to each provider feature. A value closer to 1 (e.g., a higher value) may indicate a stronger relationship between the physiological system and provider feature. For example, for physiological system 5, muscular system and provider feature, volume of patients with COPD a latent dimension of 0.013 is indicated. This may indicate that a provider with a certain level of COPD patients has a weak relationship with the muscular system.

FIG. 3H shows a table representing provider characteristics feature vector for P1. In FIG. 3H, the table illustrates the result of multiplying the provider characteristics vector shown in FIG. 3F by the provider feature matrix of learnt latent weights as shown in FIG. 3G.

In some aspects, the scoring module of server device 120 is configured to precompute the provider vector B by summing the provider-characteristic-feature vector (e.g., 3H) and a provider learnt parameters vector $F_P$ (e.g., row for P1 in 3I) to generate the respective provider vector B (e.g., row for P1 in 3J). The server device 120 may then store the respective provider vector B for later use after a request is received. As discussed above, FIG. 3H shows a table representing provider characteristics feature vector for P1. FIG. 3I shows a table representing the provider identity learnt parameters vectors for individual providers (e.g., P1, P2 and P3 also described in FIG. 3F). In this example, lower numbers indicate better correlation between latent dimensions and the respective provider. For example, provider 2 may have the greatest correlation to the renal, endocrine and muscular systems, as shown by the 0.018 value, the 0.0165 value and the 0.011 value, respectively. Provider 3 may have the greatest correlation to the respiratory, as shown by the 0.003 value. Provider 1 has the greatest correlation to the circulatory system, as shown by the 0.019 value. The server device 120 may precompute the provider vector B (e.g., 3J) for Provider 1 by summing the table representing provider characteristics feature vector for P1 in FIG. 3H with the row corresponding to the learnt parameters vector for P1 from the table in FIG. 3I. In FIG. 3J, the row corresponding to P1 in the table illustrates the result of summing the member characteristics feature vector for P1 in FIG. 3H with the learnt parameters vector for P1 in FIG. 3I.

In some aspects, before receiving the provider request, for each provider: the server device 120 precomputes a respective member-provider interaction weight C, where $$C = \sum_n \gamma_n * I_n$$

of equation (1). In some aspects, the scoring module of server device 120 is configured to precompute the member-provider interaction weight C by arranging the member-provider interaction characteristics into an interaction characteristics vector γ and computing its scalar product with the learnt interaction weight vector I. Referring to FIG. 3K there is shown a table of interaction characteristics or features for each member. Interaction features shown in FIG. 3K include number of web "clicks" on the provider's web page, number of times provider was seen in top 50 results in the past searches and number of historic visits to the provider of the same specialty. For example, member 1 may have clicked on provider 1 webpage once, member 2 may have clicked on provider 1 webpage 4 times and member 3 may have clicked on provider 1 webpage 7 times. Also shown in FIG. 3K, Provider 1 may have been seen in top 50 results in the past searches for Member 1, 7 times, whereas Provider 1 may have been seen in top 50 results in the past searches for Member 2, 5 times and for member 3, 5 times as well.

In some aspects, the scoring module of server device 120 is configured to precompute the member-provider interaction vector C by multiplying the interaction characteristics vector $\gamma$ by an interaction learnt feature vector I to generate the member-provider interaction weight C and storing the member-provider interaction weight C. Referring to FIG. 3L there is shown a table of interaction learnt weights for each interaction feature. For example, the interaction feature of number of web clicks on the provider's web page may have a learnt interaction weight of 0.0027 whereas the number of historic visits to a provider of the same specialty may have a learnt interaction weight of 0.0189. The learnt interaction weights of FIG. 3L may be multiplied by the interaction features of FIG. 3K to generate the member-provider interaction weight C.

In some aspects, the scoring module of server device 120 is configured to multiply the member vector A by the respective provider vector B to generate a respective member-provider score. In other aspects, the scoring module of server device 120 is configured to subsequently sum the result of the product of member vector A and the respective provider vector B with one or more of: (i) member-provider interaction weight C, (ii) member bias $B_M$, (iii) provider bias $B_P$, (iv) the member feature bias value representing a scalar multiplication of the member characteristics vector $\alpha$ and the member feature bias vector, and (v) the provider feature bias value representing a scalar multiplication of the provider characteristics vector f and the provider feature bias vector. FIG. 3M shows bias terms for the individual members and providers. For example, member 1, M1, may have a bias of 0.00171 and provider 2, P2, may have a bias of 0.018. Member and provider biases may be numeric values learnt in the learning phase of the algorithm. The member and provider biases represent the contribution of a member's or provider's identity itself towards the cost (or a success measure). For a provider, the provider bias may represent the general nature of the specific provider who provides consistently high or low cost of care. FIG. 3N shows bias terms for the various member and provider features. In FIG. 3N, Diabetes, COPD, heart condition and obesity are associated with the member features shown in FIG. 3A. These member feature bias terms may be multiplied by the member feature values in FIG. 3A to generate the member feature bias value. For providers, in FIG. 3N, Diabetes volume, COPD volume and heart condition volume are associated with the provider features shown in FIG. 3F. These provider feature bias terms may be multiplied by the provider features in FIG. 3F to generate the provider feature bias value.

Referring to FIG. 3O, there is shown a table of predicted scores utilizing equation (1) described above. The scores are utilized for recommending a specific provider for member 1, member 2 and member 3. In this example, a lower score may indicate a higher likelihood of recommending a particular provider. In this example, for member 1, provider 2 has a recommendation of provider 2 with a value of 1.76. Because provider 2 has the lowest score, provider 2 will have the highest ranking when the ordered list is provided to the requestor. This example also illustrates how the values change for other members. For example, for member 2, provider 3 will have the highest ranking and for member 3, provider 1 will have the highest ranking. In this example, by performing the precomputations, the final scoring for a member provider pair now only involves H multiplication operations post request, which is equal to number of latent dimensions chosen at the time of training the model for the parameters (e.g., 9 latent dimensions in the example provided herein). Such a reduction in the number of multiplication operations required after a request is received significantly increases response time for the server device 120.

The scoring module of server device 120 is configured to transmit (212) the ordered list of the providers to the member computing device via the provider search interface.

In some aspects, equation (1) may be modified to only include a subset of: member data, provider data and interaction data. For example, if interaction data is not available, an equation similar to the above equation, but removing interaction-specific variables from the loss function, may be utilized. In another example, if member data is not available, equation (1) may be modified by removing member-specific variables to define a new loss function that may be optimized. In another example, if member data and provider data is not available, equation (1) may be modified by removing member and provider specific feature variables so that the algorithms may learn from latent representations of member and provider identities. By allowing equation (1) to be modified, the server device 120 may be more adaptable to different searches with different criteria requirements.

Numerous details are described herein in order to provide a thorough understanding of the example aspects illustrated in the accompanying drawings. However, some aspects may be practiced without many of the specific details, and the scope of the claims is only limited by those features and aspects specifically recited in the claims. Furthermore, well-known methods, components, and circuits have not been described in exhaustive detail so as not to unnecessarily obscure pertinent aspects of the aspects described herein.

It will be appreciated by those skilled in the art that changes could be made to the exemplary aspects shown and described above without departing from the broad inventive concepts thereof. It is understood, therefore, that this invention is not limited to the exemplary aspects shown and described, but it is intended to cover modifications within the spirit and scope of the present invention as defined by the claims. For example, specific features of the exemplary aspects may or may not be part of the claimed invention and various features of the disclosed aspects may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A method for recommending one or more providers to a member, the method comprising:
   at a scoring module of a server:
   receiving, from a computing device via a provider search interface, a provider request including a member identifier and member specified criteria;
   retrieving one or more provider identifiers for association with the member specified criteria;
   retrieving one or more member characteristics for association with the member identifier;
   for each provider identifier, retrieving one or more provider characteristics for association with the provider identifier;
   analyzing the member characteristics and the provider characteristics to generate an ordered list of the providers, wherein the ordered list of the providers is based upon a relevancy rank of each provider that is specific to the member, wherein the relevancy rank is a function of at least one of: a provider cost factor, a provider quality factor, or a weighted combination thereof, wherein analyzing the member characteristics and the provider characteristics to generate an ordered list of the providers includes: for each of the providers, calculating a member-provider score:
   wherein M refers to the member associated with the provider request,
   wherein P refers to the provider,
   wherein α is the features associated with the member,
   wherein β is the features associated with the respective provider,
   wherein $L_i^m$ are learnt parameters of a particular success metric model associated with the member,
   wherein $L_j^p$ are the learnt parameters of a particular success metric model associated with the respective provider,
   $F_M$ is the learnt parameters (matrix) associated with and specific to the member,
   $F_P$ is the learnt parameters (matrix) associated with and specific to the respective provider,
   $B_i^m$ is the feature bias terms that are learnt for the member,
   $B_j^p$ is the feature bias terms that are learnt for the respective provider,
   $B_M$ is the bias for the member,
   $B_p$ are the bias for the respective provider,
   $\gamma_n$ is the $n^{th}$ interaction feature,
   $I_n$ is the learnt weight for the $n^{th}$ interaction feature; and
   transmitting the ordered list of the providers to the computing device via the provider search interface.

2. The method of claim 1, wherein analyzing the member characteristics and the provider characteristics includes:
   before receiving the provider request, precomputing a member vector and, for each provider, precomputing a respective provider vector and a respective member-provider interaction weight.

3. The method of claim 2, wherein precomputing the member vector includes:
   arranging the member characteristics into a member characteristics vector;
   multiplying the member characteristics vector by a member feature matrix of learnt latent weights for each of the member characteristics to generate a member-characteristic-feature vector;
   summing the member-characteristic-feature vector and a member learnt parameters vector to generate a member vector; and
   storing the member vector.

4. The method of claim 2, wherein precomputing a respective provider vector includes:
   arranging the provider characteristics for the respective provider into a provider characteristics vector;
   multiplying the provider characteristics vector by a provider feature matrix of learnt latent weights for each of the provider characteristics to generate a provider-characteristic-feature vector;
   summing the provider-characteristic-feature vector and a provider learnt parameters vector to generate the respective provider vector; and
   storing the respective provider vector.

5. The method of claim 4, wherein analyzing the member characteristics and the provider characteristics includes:
   after receiving the provider request, retrieving the member vector and retrieving the respective provider vectors for each provider in a set of providers and
   for each provider in the set of providers:
   multiplying the member vector by the respective provider vector to generate a respective member-provider score.

6. The method of claim 5, wherein analyzing the member characteristics and the provider characteristics includes:
   summing the member-provider score and a feature bias value to update the member-provider score.

7. The method of claim 6, wherein analyzing the member characteristics and the provider characteristics includes:
   ranking the providers based on the member-provider score for each of the respective providers.

8. The method of claim 1, wherein member characteristics include at least one of: previous conditions, previous diagnoses, previous procedures, member demographics, age, gender, prescription information, over-the-counter medication history, habits, search history, member interactions with a provider search interface, zip code, number of hospitalizations in a past time period, and family history.

9. The method of claim 1, wherein provider characteristics include at least one of: volume of patients seen, types of disease conditions seen, patient-submitted ratings, language, number of patients seen for each of the types of disease condition, quality of care for each of the types of disease condition, age, gender, years of practice, interactions with the member, and cost.

10. The method of claim 1, wherein member specified criteria includes at least one of: member location and member health conditions.

11. The method of claim 1, wherein the ordered list of the providers is in association with the member specified criteria.

12. The method of claim 1, wherein analyzing the member characteristics and the provider characteristics includes:
    before receiving the provider request, precomputing a member feature bias weight and a provider feature bias weight.

13. A system for recommending one or more providers to a member, the system comprising:
    one or more memory units each operable to store at least one program; and
    a server including a scoring module having at least one processor communicatively coupled to the one or more memory units, in which the at least one program, when executed by the at least one processor, causes the at least one processor to perform the steps of:

receiving, from a computing device via a provider search interface, a provider request including a member identifier and member specified criteria;

retrieving one or more provider identifiers for association with the member specified criteria;

retrieving one or more member characteristics for association with the member identifier;

for each provider identifier, retrieving one or more provider characteristics for association with the provider identifier;

analyzing the member characteristics and the provider characteristics to generate an ordered list of the providers, wherein the ordered list of the providers is based upon a relevancy rank of each provider that is specific to the member, wherein the relevancy rank is a function of at least one of: a provider cost factor, a provider quality factor, or a weighted combination thereof, wherein analyzing the member characteristics and the provider characteristics to generate an ordered list of the providers includes:

for each of the providers, calculating a member-provider score:

wherein M refers to the member associated with the provider request, wherein P refers to the provider, wherein $\alpha$ is the features associated with the member, wherein $\beta$ is the features associated with the respective provider, wherein $L_i^m$ are learnt parameters of a particular success metric model associated with the member, wherein $L_j^p$ are the learnt parameters of a particular success metric model associated with the respective provider, $F_M$ is the learnt parameters (matrix) associated with and specific to the member, $F_p$ is the learnt parameters (matrix) associated with and specific to the respective provider, $B_i^m$ is the feature bias terms that are learnt for the member, $B_j^p$ is the feature bias terms that are learnt for the respective provider, $B_M$ is the bias for the member, $B_p$ are the bias for the respective provider, $\gamma_n$ is the $n^{th}$ interaction feature, $I_n$ is the learnt weight for the $n^{th}$ interaction feature; and transmitting the ordered list of the providers to the computing device via the provider search interface.

14. The system of claim 13, wherein analyzing the member characteristics and the provider characteristics includes:

before receiving the provider request, precomputing a member vector and, for each provider, precomputing a respective provider vector and a respective member-provider interaction weight.

15. The system of claim 14, wherein precomputing the member vector includes:

arranging the member characteristics into a member characteristics vector;

multiplying the member characteristics vector by a member feature matrix of learnt latent weights for each of the member characteristics to generate a member-characteristic-feature vector;

summing the member-characteristic-feature vector and a member learnt parameters vector to generate a member vector; and storing the member vector.

16. The system of claim 14, wherein precomputing a respective provider vector includes:

arranging the provider characteristics for the respective provider into a provider characteristics vector;

multiplying the provider characteristics vector by a provider feature matrix of learnt latent weights for each of the provider characteristics to generate a provider-characteristic-feature vector;

summing the provider-characteristic-feature vector and a provider learnt parameters vector to generate the respective provider vector; and storing the respective provider vector.

17. The system of claim 16, wherein analyzing the member characteristics and the provider characteristics includes:

after receiving the provider request, retrieving the member vector and retrieving the respective provider vectors for each provider in a set of providers and for each provider in the set of providers:

multiplying the member vector by the respective provider vector to generate a respective member-provider score.

18. The system of claim 17, wherein analyzing the member characteristics and the provider characteristics includes:

summing the member-provider score and a feature bias value to update the member-provider score.

19. The system of claim 18, wherein analyzing the member characteristics and the provider characteristics includes:

ranking the providers based on the member-provider score for each of the respective providers.

20. The system of claim 13, wherein member characteristics include at least one of: previous conditions, previous diagnoses, previous procedures, member demographics, age, gender, prescription information, over-the-counter medication history, habits, search history, member interactions with a provider search interface, zip code, number of hospitalizations in a past time period, and family history.

21. The system of claim 13, wherein provider characteristics include at least one of: volume of patients seen, types of disease conditions seen, patient-submitted ratings, language, number of patients seen for each of the types of disease condition, quality of care for each of the types of disease condition, age, gender, years of practice, interactions with the member, and cost.

22. The system of claim 13, wherein member specified criteria includes at least one of: member location and member health conditions.

23. The system of claim 13, wherein the ordered list of the providers is in association with the member specified criteria.

24. The system of claim 13, wherein analyzing the member characteristics and the provider characteristics includes: before receiving the provider request, precomputing a member feature bias weight and a provider feature bias weight.

* * * * *

UNITED STATES PATENT AND TRADEMARK OFFICE
CERTIFICATE OF CORRECTION

PATENT NO. : 10,353,908 B1
APPLICATION NO. : 16/234918
DATED : July 16, 2019
INVENTOR(S) : Lakshmi Manohar Akella et al.

It is certified that error appears in the above-identified patent and that said Letters Patent is hereby corrected as shown below:

On the Title Page

Item (12), delete "Aella" and insert --Akella--.

Item (72), under Inventors, delete "Lakshmi Manohar Aella" and replace with --Lakshmi Manohar Akella-- and delete "CT" from Adarsh Ramesh's residence and replace with --IL--.

In the Claims

Column 17, Claim 1, Line 32, after "score", please insert the following:

-- $$Score(M,P) = \left(\sum_i \alpha_i * L_i^m + F_M\right)^T \left(\sum_j \beta_j * L_j^p + F_P\right) + \sum_k \alpha_i B_i^m + \sum_l \beta_l B_l^p + B_M + B_P + \sum_n \gamma_n * I_n$$ --.

Column 19, Claim 13, Line 25, after "score", please insert the following:

-- $$Score(M,P) = \left(\sum_i \alpha_i * L_i^m + F_M\right)^T \left(\sum_j \beta_j * L_j^p + F_P\right) + \sum_k \alpha_i B_i^m + \sum_l \beta_l B_l^p + B_M + B_P + \sum_n \gamma_n * I_n$$ --.

Signed and Sealed this
Twenty-seventh Day of August, 2019

Andrei Iancu
*Director of the United States Patent and Trademark Office*